United States Patent [19]
Freud et al.

[11] Patent Number: 5,650,571
[45] Date of Patent: Jul. 22, 1997

[54] LOW POWER SIGNAL PROCESSING AND MEASUREMENT APPARATUS

[76] Inventors: Paul J. Freud, 3113 Cloverly Dr., Furlong, Pa. 18925; Michael N. Trainer, 186 Fretz Rd., Telford, Pa. 18969; Giancarlo Punis, 112 Brittany Dr., Chalfont, Pa. 18914; Anthony M. Demark, 700 Gawain Rd., Chymonth Meeting, Pa. 19462

[21] Appl. No.: 403,517

[22] Filed: Mar. 13, 1995

[51] Int. Cl.⁶ .................. G01F 1/712; G01F 1/66
[52] U.S. Cl. .................. 73/861.06; 73/861.18; 73/861.28
[58] Field of Search .................. 73/627, 628, 632, 73/861.06, 861.18, 861.21, 861.25, 861.26, 861.27, 861.29, 861.28

[56] References Cited

U.S. PATENT DOCUMENTS

| | | | |
|---|---|---|---|
| H609 | 3/1989 | Higgins et al. | 377/61 |
| 3,621,221 | 11/1971 | Cann | 235/181 |
| 3,762,221 | 10/1973 | Coulthard | 73/861.06 |
| 3,819,919 | 6/1974 | McGinigle | 73/861.06 |
| 3,845,660 | 11/1974 | McDonnell | 73/861.06 |
| 3,946,342 | 3/1976 | Hartmann | 333/72 |
| 4,019,038 | 4/1977 | Critten et al. | 235/181 |
| 4,035,628 | 7/1977 | Lampe et al. | 235/193 |
| 4,079,238 | 3/1978 | Lampe et al. | 364/824 |
| 4,201,083 | 5/1980 | Kurita et al. | 73/194 |
| 4,223,270 | 9/1980 | Schmid et al. | 328/112 |
| 4,232,548 | 11/1980 | Baumoel | 73/861.28 |
| 4,248,085 | 2/1981 | Coulthard | 73/861.06 |
| 4,257,275 | 3/1981 | Kurita et al. | 73/861.06 |
| 4,267,580 | 5/1981 | Bond et al. | 364/824 |
| 4,331,025 | 5/1982 | Ord, Jr. | 73/861.28 |
| 4,397,193 | 8/1983 | Ryan et al. | 73/861.28 |
| 4,402,230 | 9/1983 | Raptis | 73/861.06 |
| 4,478,088 | 10/1984 | Loveland | 73/861.28 |
| 4,480,485 | 11/1984 | Bradshaw et al. | 73/861.28 |
| 4,494,213 | 1/1985 | Thompson | 364/604 |
| 4,507,974 | 4/1985 | Yelderman | 73/861.06 |
| 4,598,593 | 7/1986 | Sheen | 73/861.04 |
| 4,604,904 | 8/1986 | Massen | 73/861.06 |
| 4,708,021 | 11/1987 | Braun et al. | 73/861.06 |
| 4,760,743 | 8/1988 | Clifford et al. | 73/861.06 |
| 4,787,252 | 11/1988 | Jacobson et al. | 73/861.28 |
| 4,841,780 | 6/1989 | Inada et al. | 73/861.06 |
| 4,912,519 | 3/1990 | Yoshida et al. | 73/861.06 |
| 4,930,358 | 6/1990 | Motegi et al. | 73/861.28 |

(List continued on next page.)

FOREIGN PATENT DOCUMENTS

| | | |
|---|---|---|
| 0 179 541 | 4/1986 | European Pat. Off. . |
| 0 262 441 | 4/1988 | European Pat. Off. . |
| WO83/03897 | 11/1983 | WIPO . |
| WO85/00653 | 2/1985 | WIPO . |

OTHER PUBLICATIONS

PCT International Search Report dated Oct. 25, 1996—International Application No. PCT/US96/03378 (7 pps.).
A.G. Milnes, *Semiconductor Devices and Integrated Electronics*, published by Van Nostrand Reinhold Company, pp. 590–598 and 610–617.
D.T. Bell, Jr., and L.T. Claiborne, "Phase Code Generators and Correlators", Texas Instruments, Inc., Dallas, Texas, pp. 307–316.

*Primary Examiner*—Hezron E. Williams
*Assistant Examiner*—Helen C. Kwok

[57] ABSTRACT

A low power apparatus for measuring various process parameters and/or physical properties of a fluid or gas medium by measuring the change of a wave signal or time dependent signal as it traverses the fluid or gas medium, the apparatus comprising: at least one transmission transducer for providing a transmitted wave or time dependent signal for injection into the fluid or gas medium; at least one reception transducer, displaced from the transmission transducer for receiving a received wave or time dependent signal from the fluid or gas medium; and an analog signal processor, coupled to the reception transducer, for processing of the received wave or time dependent signal such that a short interval of the processed received wave or time dependent signal is extracted.

17 Claims, 5 Drawing Sheets

U.S. PATENT DOCUMENTS

| | | | |
|---|---|---|---|
| 4,976,154 | 12/1990 | Schneider et al. | 73/861.06 |
| 5,012,449 | 4/1991 | Todd | 73/861.18 |
| 5,029,481 | 7/1991 | Keech | 73/861.06 |
| 5,060,506 | 10/1991 | Douglas | 73/24.01 |
| 5,121,639 | 6/1992 | McShane | 73/861.06 |
| 5,224,482 | 7/1993 | Nikoonahad | 128/661.08 |
| 5,336,957 | 8/1994 | Yamanouchi et al. | 310/313 D |

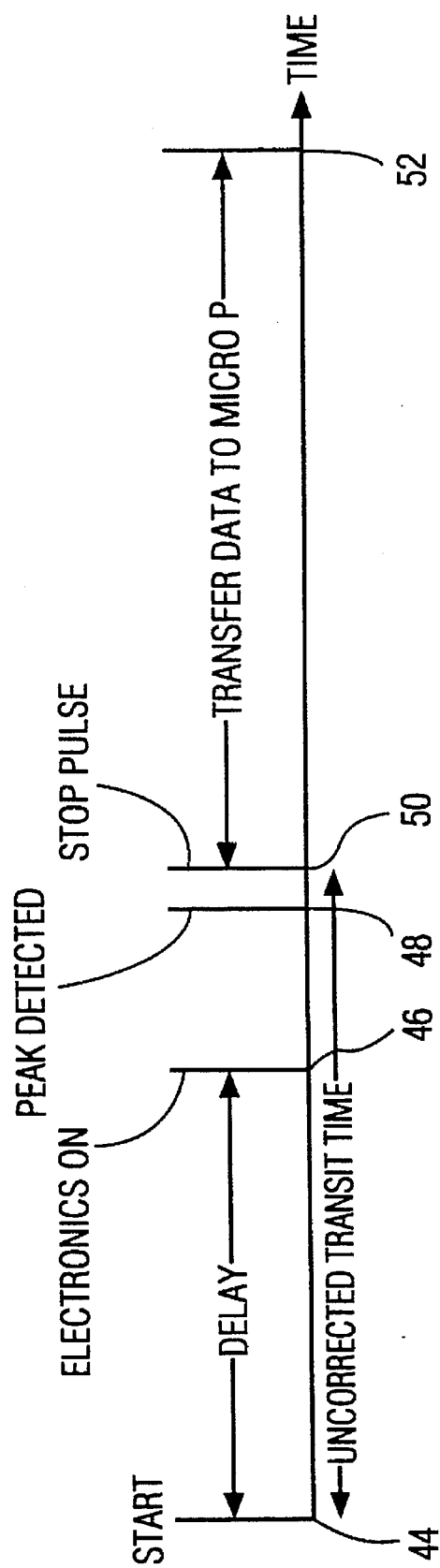

LOW POWER SIGNAL PROCESSING AND MEASUREMENT APPARATUS

The present invention relates generally to measurements of process parameters under conditions of very low power consumption such that the measurement apparatus can be operated as a field instrument and be powered by the low power available from the electrical supply of the low power connection. More particularly, the present invention relates to measurements which require extensive processing of signals with a wave or time dependent nature in order to measure the process parameters and/or physical properties of a medium of interest. One such device is a flow measurement apparatus capable of measuring the transit time of ultrasonic signals through a fluid or gas medium and analyzing the transit time to determine the flow rate of the medium.

BACKGROUND OF THE INVENTION

The measurement of process parameters or physical properties of a medium by field instruments is preferably performed by utilizing low power 4–20 milliamp (ma) two wire transmitters or an equivalent low power information transmittal system. The low power operation affords instruments which are intrinsically safe in hazardous conditions and minimize the amount of wiring required to install the measurement instrument. A number of measurements require the processing of wave signals in order to obtain the most accurate and reliable of results.

A reliable and accurate means of performing the signal processing is to use digital signal processing techniques which have become readily available in recent years with the advent of microprocessors and digital signal processors. One of the characteristics of devices which perform digital signal processing is the high power required to perform the required signal processing and the data intensive nature of digital signal processing operations. However, the high power requirements of digital signal processing are incompatible with low power field instrument transmitters.

For example, the measurement of the flow velocity of a fluid in a conduit can be accomplished by transmitting ultrasonic pulses through the flowing fluid as it travels through the conduit or pipe and measuring the transit time of these ultrasonic pulses. The direction of propagation of the ultrasonic pulse is arranged so that the transit time is measured in the direction of flow (downstream) where it is decreased by the flow and opposite the direction of flow (upstream) where it is increased by the flow. The transit time is measured in both directions and the difference between the upstream and down stream transit times is used to determine the flow velocity.

A number of different techniques have been employed to accurately measure the transit time of ultrasonic pulses across a fluid containing conduit. For a typical measurement technique, the sound velocity of a propagated ultrasonic pulse is much greater than the fluid velocity and, thus, the transit time of the ultrasonic pulse is only slightly changed by the fluid velocity, thereby requiring the use of very sensitive equipment capable of detecting such slight changes in ultrasonic pulse transit times between a transmitter and a receiver. Flow meter instrumentation manufacturers have continuously attempted to develop equipment and systems which provide increased accuracy in the measuring of the transit time and flow velocity of fluid passing through conduits.

Early schemes transmitted ultrasonic waveforms through the moving fluid and analyzed the received ultrasonic waveforms to determine the flow rate of the fluid. For example, U.S. Pat. No. 4,787,252, which issued Nov. 29, 1988, provides a flow meter that transmits a signal modulated with a particular code through a fluid or gas medium. Then, the flow meter correlates the received signal with its originating transmitted signal to produce a correlation function having a peak at a time equal to the propagation time. The correlation function is determined by correlating, i.e., lining up, the signal pattern of the received signal with the known pattern of the transmitted signal. This scheme provides a highly accurate determination of the arrival time of the transmitted signal despite the presence of noise.

The amount of energy consumption of a flow measurement apparatus or flow meter is of great concern to a user, particularly for a battery-powered system, a two wire 4–20 ma transmitter system, a low power digital field bus system or an equivalent low power communication scheme. The flow meter disclosed in U.S. Pat. No. 4,787,252 consumes an excessive amount of energy before correlating the received signal. This is because such a flow meter uses a fast analog-to-digital converter (ADC) to digitize the electrical analog signal received by the receiving transducer. The ADC then transmits the digitized data to a memory circuit and direct memory access (DMA) controller which consume additional power. Thereafter, the digitized data held in the memory circuit and DMA is transmitted to a correlator (i.e., a microprocessor) which is capable of multiplying all of the digitized data point against the number of pulses which were generated in order to determine the flow rate of the fluid medium passing through the conduit or pipe.

As such, the flow meter of U.S. Pat. No. 4,787,252 consumes substantial amounts of energy during the analog-to-digital conversion, memory circuit, DMA and correlation steps making it undesirable for many low power in the field applications. Moreover, a reasonably powerful microprocessor is required to perform the correlation operation when individual digitized points are continuously being sent to the microprocessor. For example, the pattern of the coded transmission signal could be defined by 50 numbers sampled from a 5 cycle pulse of a 1 MHz signal. The electrical received analog signal might be scanned over a time interval of 50 microseconds to assure that the pulse is received. The scanned signal is converted to 500 digitized signals via an ADC device before being sent to the microprocessor for correlation calculation to obtain the flow rate of the fluid or gas medium passing through a conduit or pipe. The correlation operation that takes place within the microprocessor involves 50 multiplications performed 500 times or 25000 multiplications. This correlation operation would not be a problem for high power microprocessors with ample memory and high speed. However, when attempting to conserve power for in the field applications, the correlation operation does present a problem since low power flow detectors necessitate a substantial lowering of the speed of the microprocessor operation, thereby causing the calculations to take an inordinate amount of time producing a flow rate for a specific period of time. The extensive correlation calculations required by conventional flow rate detectors are also not suitable for low power detectors since the reduced speed of the microprocessor contained therein would also not allow for real-time detection of the flow rate of the fluid or gas medium passing through the conduit or pipe. These correlation calculations would also use substantial amounts of an already limited energy supply, thus effecting the overall performance of the detector itself.

The present invention provides a measurement apparatus which avoids the high power digital signal processing means while retaining the accuracy and reliability of the signal process function of the conventional digitized detectors. That is, the present invention overcomes the large power requirements of the conventional detector discussed above by compressing the amount of digitized data needed to determine the arrival time of an electrical received analog signal and calculate the flow velocity, distance, or other properties of the fluid or gas medium in order to minimize energy consumption.

The present invention provides a measurement apparatus which is capable of performing the correlation operation while the electrical received signal is in analog form such that a single output peak is produced from the analog correlator, thereby substantially reducing the number of samples of the analog signal which must be converted to a digitized form by an analog-to-digital converter (ADC) disposed between the analog correlator and a microprocessor. As such, the microprocessor is only needed to calculate the correlation peak time position, the transit time, the flow velocity, fluid or gas level or other physical properties of a fluid or gas medium from the few digitized data points transmitted from the ADC rather than perform extensive multiplication of numerous digitized data points as required in conventional flow rate detectors.

The present invention provides a measurement apparatus which is capable of determining exactly the time interval containing the peak value of the correlation of the received analog signal so as to clearly to identify and extract the correlation signal during the identified time interval, hereinafter referred to as the peak interval. This novel measurement apparatus limits the amount of digital information required for accurate determination of the transit time of an ultrasonic signal in a flow measurement operation, thereby reducing the multiplication operations previously required to calculate the transit time, and enabling such accurate and full measurements to be determined at a very low power consumption.

SUMMARY OF THE INVENTION

The present invention, in brief summary, is a low power apparatus for measuring various process parameters and/or physical properties of a fluid or gas medium by measuring the change of a wave signal or time dependent signal as it traverses the fluid or gas medium. This apparatus comprising: at least one transmission means for providing a transmitted wave or time dependent signal for injection into the fluid or gas medium; at least one reception means, displaced from the transmission means for receiving a received wave or time dependent signal from the fluid or gas medium; and means, coupled to the reception means, for analog signal processing of the received wave or time dependent signal such that a short interval of the processed received wave or time dependent signal is extracted.

Another embodiment of the present invention includes an apparatus for measuring flow velocity, level or other physical properties of a fluid or gas medium by measuring a transit time of an ultrasonic pulse through the fluid or gas medium, that comprises transmission means for providing an ultrasonic transmission signal for injection into the fluid or gas medium at a predetermined time; reception means, displaced from the transmission means, for receiving an ultrasonic received analog signal from the fluid or gas medium; and means, coupled to the reception means, for correlating the ultrasonic received analog signal with the ultrasonic transmission signal such that a peak interval of the correlation of the ultrasonic received analog signal is extracted, whereby there is obviated the large amount of digital data usually required to be processed for calculating the transit time.

The transmission means of the apparatus for measuring includes at least one transmitting ultrasonic transducer which is capable of injecting an ultrasonic pulse into the fluid or gas medium and, likewise, the reception means includes at least one receiving ultrasonic transducer for receiving the ultrasonic received analog signal which is the result of the ultrasonic pulse traveling through the fluid or gas medium.

The means, coupled to the reception means, for correlating the ultrasonic received analog signal with the ultrasonic transmission signal preferably comprises an analog correlator capable of generating a singular analog peak output based on an alignment of the ultrasonic received analog signal with the ultrasonic coded transmission signal, the peak output is included in the peak interval, and an analog shift register, coupled to the means for correlating, for extracting the peak interval from the correlator peak output. The analog correlator may be any charge transfer device, such as a bucket brigade device (BBD) correlator, a charge coupled device (CCD) correlator or a surface acoustic wave (SAW) correlator, which is capable of correlating the ultrasonic received analog signal with the ultrasonic transmission signal.

The measurement apparatus according to the present invention further comprises a peak detector, responsive during the peak interval, for signaling to the analog shift register to extract a particular time period of the correlator output, wherein the particular time period includes the peak interval. The peak detector includes a stop counter which allows the analog correlator output to be transferred to the analog shift register for an interval to include the peak interval.

An analog-to-digital converter (ADC) which is coupled to the analog shift register such that the analog correlation signal of the peak interval which is stored on the analog shift register can be digitized. A microprocessor running at low frequency and therefore at low power is then coupled to the ADC for transferring the peak interval data stored on the analog shift register to the microprocessor memory where calculation is performed from the digitized peak interval of the transit time, flow rate or velocity, or level of the fluid or gas medium. The calculation of the transit time is made by adding all of the set delay times to the calculated correlation peak position. As stated above, the peak can be defined by 10 digitized points and the exact position of the peak maximum is calculated by curve fitting to the 10 points. Thus, the transit time of an ultrasonic pulse traveling through a fluid or gas medium can be calculated in accordance with the below equation:

$$\text{transit time} = t(\text{delay}) + t(\text{peak interval}) + t(\text{curve fit})$$

The velocity of flow is calculated using the equation set forth below which relates the difference in upstream and downstream transit times, tup and tdown, respectively, sound velocity in the medium at rest (C) and path length (L) to the flow velocity (V):

$$V(\text{flow}) = (\text{tup} - \text{tdown}) \times C^2 / 2L$$

The measurement apparatus further comprises a delay counter for delaying the activation of the any of the following: analog correlator, analog shift register, peak detector, analog-to-digital converter, and microprocessor. The purpose of the delay counter is to delay the activation in order to conserve energy. The time delay is predetermined by the microprocessor and is dependent on the sound velocity of the medium and on the size of the passage through which the fluid or gas medium travels or is contained. Also provided is a clock timer is for the purpose of providing timing to the transmission means and the analog correlator, the delay means, and the peak detection means.

The low power measurement apparatus of the present invention can be used for numerous applications, such as determination of flow rate or velocity of a fluid or liquid medium, measuring the fluid or gas medium level in a fixed tank, and for determining the compositional make-up of a binary mixture of fluids or gases. It is contemplated that the low power measurement apparatus of the present invention can also be used in any situation where the transit time of a peak interval generated from a coded signal or pulse can be detected.

A low power apparatus for measuring flow velocity comprises a means for measuring a transit time of an ultrasonic pulse through the fluid or gas medium both with and against the flow of the fluid or gas medium. The means for measuring the transit time preferably comprises: a first transmission means for providing a first ultrasonic transmission signal for injection into the fluid or gas medium in the direction of the flow at a predetermined time; a first reception means, displaced from the first transmission means, for receiving a first ultrasonic received analog signal from the fluid or gas medium; a second transmission means for providing a second ultrasonic transmission signal for injection into the fluid or gas medium in the direction against the flow at a predetermined time; a second reception means, displaced from the second transmission means, for receiving a second ultrasonic received analog signal from the fluid or gas medium; and means, coupled to both the first and second reception means, for correlating the first and second ultrasonic received analog signals with the first and second ultrasonic transmission signals, respectively, such that peak intervals of the correlation of both the first and second ultrasonic received analog signals are extracted, whereby there is obviated the large amount of digital data usually required to be processed for calculating the transit time. The flow velocity is determined from the formula:

$$\text{Flow Velocity} = \text{Transit Time Change} \times ((\text{Sound Velocity}^2/2) \times \text{Path Length})$$

The preferred level detector comprises: transmission means for providing an ultrasonic transmission analog signal for injection into the fluid or gas medium at a predetermined time; reception means for receiving an ultrasonic received analog signal from the fluid or gas medium; and means, coupled to the reception means, for correlating the ultrasonic received analog signal with the ultrasonic transmission analog signal such that a peak interval of the ultrasonic received analog signal is extracted. Furthermore, this level detector comprises a means connected to the correlating means which is capable of determining the position of the phase interface within the container by determining the transit time of the ultrasonic transmission analog signal through either the gas or fluid medium from the peak interval of the ultrasonic received analog signal. The level is determined through the formula:

$$\text{Level} = \text{Sound Velocity}/\text{Transit Time}$$

It is also possible to measure the velocity of a binary mixture comprising either a fluid or gas medium to determine the compositional make-up of the binary mixture by measuring a transit time of an ultrasonic pulse through the binary mixture as provided in the present invention. Such a compositional make-up detector preferably comprises: transmission means for providing an ultrasonic transmission analog signal for injection into the binary mixture at a predetermined time; reception means, displaced from the transmission means, for receiving an ultrasonic received analog signal from the binary mixture; and means, coupled to the reception means, for correlating the ultrasonic received analog signal with the ultrasonic transmission analog signal such that a peak interval of the ultrasonic received analog signal is extracted, whereby there is obviated the large amount of digital data usually required to be processed for calculating the transit time. Furthermore, the compositional make-up detector also comprises a means connected to the correlating means which is capable of determining the velocity of the binary mixture by determining the transit time of the ultrasonic transmission analog signal through either the binary mixture from the peak interval of the ultrasonic received analog signal. The composition of the mixture is calculated using the general formulas set forth below:

$$\text{Proportion A} = (\text{velocity(mix)} - \text{velocity B})/(\text{velocity A} - \text{velocity B})$$

$$\text{Proportion B} = (\text{velocity(mix)} - \text{velocity A})/(\text{velocity A} - \text{velocity B})$$

wherein velocity (mix) is equal to the path length divided by the transit time.

The foregoing and still further the objects and advantages of the present invention will be more apparent from the following detailed explanation of the preferred embodiments of the invention in connection with the accompanying drawings.

BRIEF DESCRIPTION OF THE DRAWINGS

FIG. 3 is a timing diagram of the preferred embodiment of FIG. 1;

DETAILED DESCRIPTION OF THE PREFERRED EMBODIMENT

Figure 1:
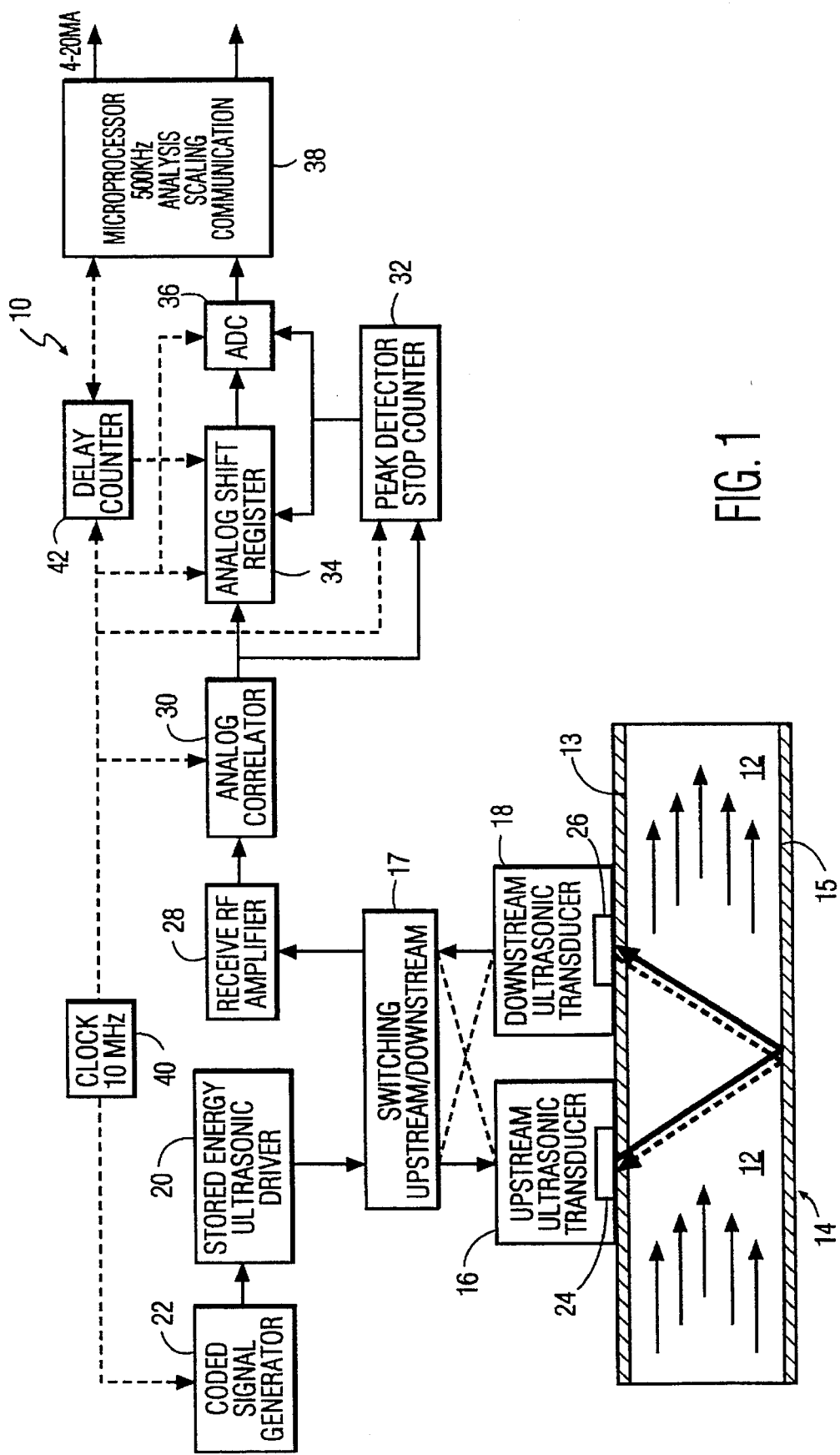
FIG. 1 is a block diagram of the preferred embodiment of the present invention.

Referring to the drawings, there is provided an ultrasonic flow measurement apparatus of the preferred embodiment which is generally represented by reference numeral 10. Referring, in particular, to the block diagram of FIG. 1, ultrasonic flow measurement system or apparatus 10 has various circuit components that determine the flow velocity of a fluid or gas medium 12 passing through a pipe or conduit 14. An ultrasonic upstream transducer 16 is mounted on an outer surface of side wall 13 of conduit 14, and an ultrasonic downstream transducer 18 is also mounted on the outer surface of side wall 13, but displaced from upstream transducer 16.

A switching means 17 is inserted between transducers (16,18) so that they can be interchanged in function. The upstream transducer 16 can be switched from being the transmitting transducer to the receiving transducer and the downstream transducer 18 can be switched from being the receiving transducer to the transmitting transducer. In this manner the upstream and downstream transit times can be measured by switching the functions of transducers (16,18).

As shown in FIG. 1, a stored energy ultrasonic drive 20 for storing energy by means of a capacitor fed by the input current for the circuit of flow measurement system 10 is provided. Ultrasonic drive 20, which is coupled to transducers (16,18) by means of switching means 17, allows high instantaneous power usage to drive either transducer 16 or 18, as well as other circuit components, with low average power through low duty factor on-off power management. Transducers (16,18) are typically manufactured of the readily obtainable piezoelectric materials such as lithium niobate, lithium tantalate, lead zirconate tantalate or quartz to mention a few.

The stored energy of ultrasonic drive 20 is gated on and off to the transmitting transducer (16 or 18) by a coded signal generator 22. The gating sequence of signal generator 22 will be at the desired frequency, preferably 1 MHz. The phase of the gated signal is periodically shifted 180 degrees to form a phase shifted code. Thus, ultrasonic driver 20 sends a coded transmission signal to the transmitting transducer (16 or 18) based on the signals received from coded signal generator 22.

When switched to its transmitting mode upstream transducer 16 includes a transmitting piezoelectric device 24 that converts the coded transmission signal received from ultrasonic driver 20 into an ultrasonic transmission signal or wave. The ultrasonic transmission signal transmitted by piezoelectric device 24 is directed through a first side wall 13 of conduit or pipe 14 into fluid or gas medium 12 which is traveling through conduit 14. The path of the ultrasonic transmission signal has a component in the direction of the flow so that its velocity is increased or decreased by the action of the flowing fluid or gas medium 12. If the path is from upstream transducer 16 to downstream transducer 18, then the flow decreases the transit time. If the path is from downstream transducer 18 to upstream transducer 16 the flow increases the transit time. In the upstream to downstream switched position the ultrasonic received analog signal is deflected off of a second side wall 15 of conduit 14 before being received by piezoelectric device 26 of downstream transducer 18 and is converted by transducer 18 to an electrical received analog signal.

The ultrasonic transmission signal is generally attenuated while traversing conduit 14 due to scattering and absorption of its ultrasonic energy as it propagates through side wall 13 of conduit 14 and fluid or gas medium 12 and reflects from side wall 15 of conduit 14. The electrical received analog signal is optionally amplified by a receive RF amplifier 28 to raise the electrical received analog signal to a voltage level adequate for subsequent analog correlation followed by analog-to-digital conversion and analysis.

The electrical received analog signal is fed to a correlator means, comprising an analog correlator 30, analog shift register 34 and peak detector 32, for performing an analog correlation and for extracting the peak interval. Typically the peak interval is one period of the received signal or 1 microsecond in the case of a 1 MHz signal. The analog correlation operation is accomplished by cross-correlating between the patterns or codes of the ultrasonic transmission signal and the electrical received analog signal.

The analog correlation operation within analog correlator 30 can be performed using a variety of correlating devices, such as, but not limited to, a Bucket Brigade Device (BBD) correlator, a Charge Coupled Device (CCD) correlator, or a Surface Acoustic Wave (SAW) correlator. These correlators have a common mode of functioning. The received and coded signal is sent to the input of the correlator. The time variation of the signal progresses through the device and at any point in time a representation of the signal over a past interval of time is stored in the device. The amount stored depends on the device details but it will be a fixed interval of a past signal. These devices also provide that points along the stored interval are sampled and the signals from these points are weighted and summed together to give the output of correlator 30. The pattern of the weightings is the same as the code imparted to the transmitted ultrasonic signal. The output signal from correlator 30 is the correlation of the electrical received analog signal and the ultrasonic transmitted signal. The correlation reaches a maximum value when the received coded signal (i.e., the electrical received analog signal) aligns with the coded points on correlator 30.

Figure 2:
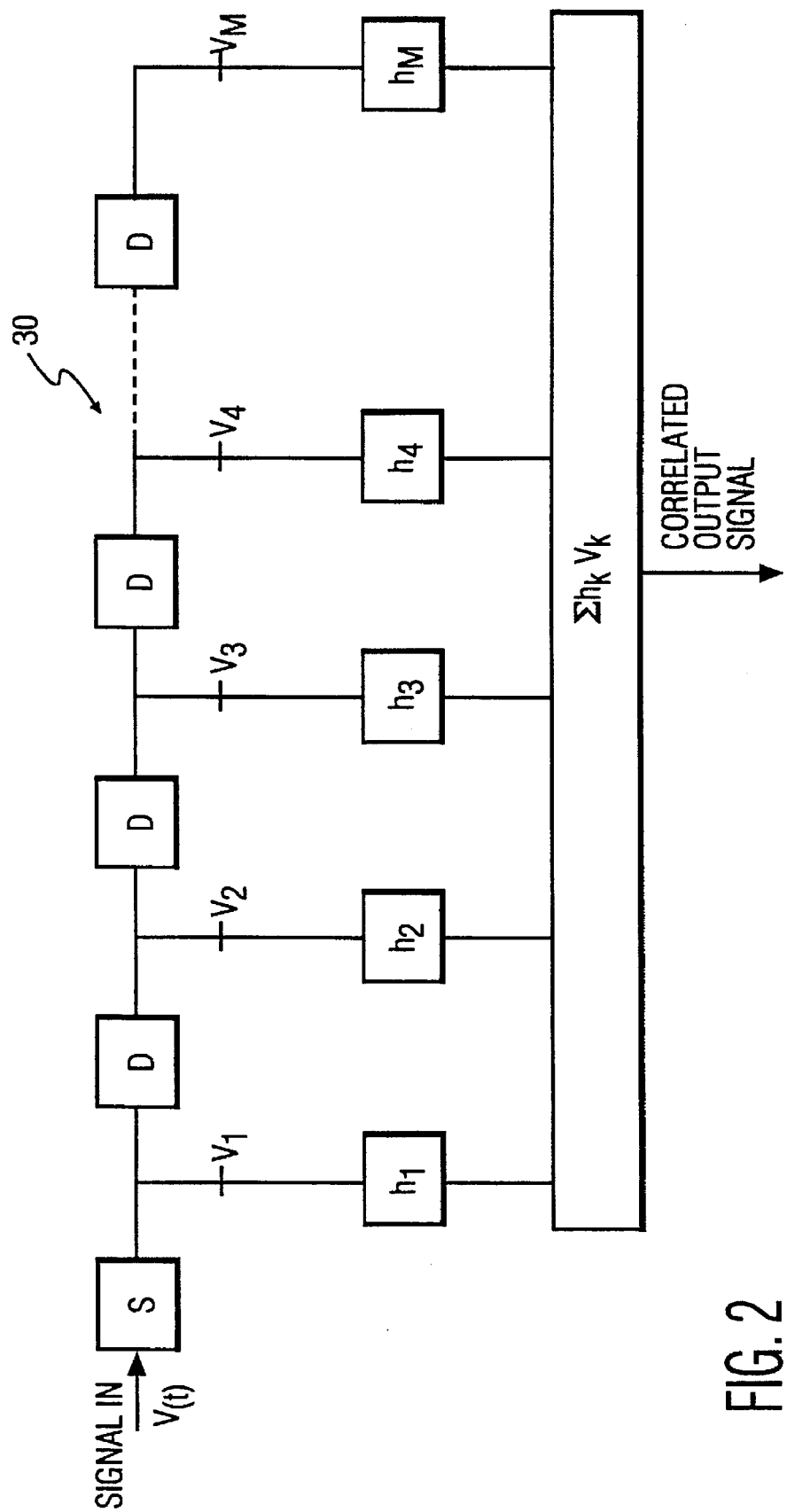
FIG. 2 is a simplified diagram of the correlator of FIG. 1.

Referring to FIG. 2, correlator 30 is a charge transfer device, such as a Bucket Brigade Device (BBD), and requires power and clocking signals for its dynamic operation. The electrical received analog signal is sampled every clock cycle and a charge proportional to the signal is injected and stored on the first of a string of MOS capacitors D on the BBD correlator. At each clock pulse the charge is passed to the next capacitor D down the string and a new signal sample is injected into the beginning of the string. After an interval of sampling the signal is stored along the string of capacitors D. At each clock cycle the interval stored shifts one clock cycle. The correlation is performed by tapping into each storage point by means of $V_1$ through $V_m$ and scaling (i.e., amplifying) with scale factors $h_1$ to $h_m$ the signal and summing all the scaled signals. The output of the BBD correlator is the sum of the scaled signals, i.e., $\Sigma h_k V_k$. As an alternative to amplifier scaling the capacitors along the string can have different capacitance values. This also scales according to the capacitance and the taps are summed with unity gain.

A CCD correlator operates in a similar way to the BBD correlator except that the capacitor structure is more complex and is in general buried in the silicon as opposed to being on the surface as with the BBD.

Background information regarding charge-transfer devices, such as BBD's and CCD's, can be found in an article by A. G. Milnes entitled *Semiconductor Devices and Integrated Electronics*, published by Van Nostrand Reinhold Company, pp. 590–598 and 610–617, which is incorporated by reference herein.

The SAW correlator performs the same function as the BBD or CCD correlator but operates on a different principle. The SAW correlator is a passive device requiring only the input signal (i.e., the electrical received analog signal) to provide an output correlation signal. The time varying input signal excites a surface acoustic wave in the strip of piezoelectric material of the SAW device. The wave with amplitude proportional to the input signal traverses the length of the device. At any instant in time the signal is represented as a wave distributed along the SAW surface. This is analogous to the charges being distributed along the string of capacitors of the BBD and CCD correlators. At various points along the SAW device surface electrode taps are placed and connected to a common summing electrode. When the wave passes the electrode tap the tap receives a voltage from the underlying piezoelectric material. The position and shape of the electrodes determine the way in which the wave points are weighted. As with the BBD and CCD correlators, if the weightings are representative of the transmitted code then the output of the SAW will represent the correlation. When the wave pattern on the SAW device surface aligns with the surface electrode pattern the correlation will be at a maximum.

Background information regarding SAW correlators can be found in an article by D. T. Bell, Jr., and L. T. Claiborne entitled "Phase Code Generators and Correlators", Texas Instruments, Inc., Dallas, Tex., pp. 307–316, which is incorporated by reference herein.

Referring again to FIG. 1, the output of correlator 30 is low until the signal is received by the receiving transducer. Then, when the pattern of the electrical received analog signal aligns with same pattern embedded in the correlator, i.e., the coded transmission signal, the output of correlator 30 will produce a maximum or peak output.

To accurately determine the time position of the correlation peak, the correlator output from analog shift register 34 is digitized by ADC 36 describe hereinafter at a faster rate than the frequency of the electrical received analog signal. For such a scheme, the digital data or points are taken at a high rate for a long period of time which is required to account for the uncertainty in locating the peak interval. These points are stored and then, eventually, transmitted to a processing means. However, time and energy can be saved by storing only the few points during the peak interval necessary to define the exact position of the correlation peak For the preferred embodiment, analog peak detector 32 which is coupled to the output of correlator 30 determines the timing for obtaining the peak interval. When the output of correlator 30 crosses a threshold value, set for a value that accommodates the expected range of values of correlation peak amplitude, peak detector 32 generates a timing signal to stop the correlation means when the entire peak interval is obtained. Only a few points of data on either side of a peak are required for an accurate determination of the peak position. Thus, peak detector 32 generates a timing signal to limit the amount of digital information required for an accurate determination of the transit time of an ultrasonic received analog signal in flow measurement apparatus 10 and to do so with very low power consumption.

The output of correlator 30 peaks, within a peak interval, when the pattern of the received analog signal aligns with the pattern of the coded transmitted signal which has been previously embedded in correlator 30. Analog peak detector 32 monitors the output from correlator 30 and produces a pulse when the peak interval is detected. The pulse activates a counter, which is part of peak detector 32, that continues the measurement for a short time following the detection of the peak interval. The measurement continues for a predetermined time to define the following edge of the peak from the output of correlator 30. After that predetermined time, a final stop signal is transmitted from peak detector 32 to analog shift register 34 and the correlation measurement is terminated.

The peak output of correlator 30 is fed into analog shift register 34. Signals coming from the output of correlator 30 is be clocked into shift register 34. At each clock pulse, a new value of the peak output is passed into shift register 34, thereby shifting the previously delivered points down the shift register. If the number of points added to shift register 34 exceeds the number of point positions available, then the earlier points will be shifted off the end of the register and discarded.

Peak detector 32 determines which points are stored in analog shift register 34 when the final stop signal occurs. For example, if shift register 34 has twenty points then the peak detector 32 would allow ten more clock cycles to occur and ten more points to be added to shift register 34. In this manner, the peak interval would be stored in shift register 34 with ten points defining the leading edge and ten points defining the following edge. The number of points retained will depend upon the choice of clock frequency and the size of the register. For the preferred embodiment, a clock frequency of 10 MHz and an ultrasonic frequency of 1 MHz is used. Therefore, these clock and ultrasonic frequencies would result in a 1 microsecond wide peak interval defined by ten points, with an additional five points on either side of the peak interval.

Analog peak detector 32 is one of the components that contributes to the overall low power scheme of the flow measurement apparatus 10. Without the critical peak detection by peak detector 32, all of the output of correlator 30 would have to be digitized by a subsequent analog-to-digital converter before transfer to a processing circuit, such as a microprocessor. Such digitizing and processing would require a far greater amount of time to account for the uncertainty in the time position of the correlated peak. Thus, by limiting the points of the output from correlator 30 to be processed, specifically to the peak interval, the amount of time the components are used and the energy consumed is minimized.

The peak interval is stored in analog shift register 34 and is subsequently digitized by an analog-to-digital converter (ADC) 36 and fed to a microprocessor 38. ADC 36 and microprocessor 38 operate at the same predetermined clock rate. This clock rate is typically low, such as on the order of 0.5 MHz., so that power consumption will be minimized. At this clock rate, the stored twenty point signal would be transferred to a memory portion of microprocessor 38 in approximately eighty microseconds, assuming two cycles per reading/transfer. For the preferred embodiment, a curve fitting analysis by microprocessor 38 would take approximately 1 millisecond to determine the peak position.

Referring to FIGS. 1 and 3, a clock 40 controls the timing of the flow measurement apparatus 10. For the preferred embodiment, clock 40 runs at 10 MHz. At the start of a measurement cycle, the transmission signal is initiated and clock 40 and delay counter 42 start counting from time line 44. The components of the flow measurement apparatus 10 that are on the receiving end, i.e., are not powered at this point to conserve energy. These receiving end components include receiver amplifier 28, correlator 30, peak detector 32, analog shift register 34, ADC 36 and microprocessor 38. When delay counter 42 reaches the end of its predetermined counting time, the receiving end components are powered on at time line 46. The delay time of delay counter 42 is calculated roughly from the known geometry of conduit 14 and sound velocity of fluid 12 and is set by a delay time signal from microprocessor 38 where this information resides in memory. The delay accommodates any uncertainty in transit time and any time required for the signal receiving components to power up when they are switched to the "on" position.

Another counter, included within peak detector 32, starts counting at time location 46 after the delay time of delay counter 42 until peak detector 32 senses the peak interval at time location 48. As described above, ten cycles of clock 40 are added to the time location 48 to determine the time location 50 of the points of the peak output in shift register 34. Thereafter, the clock of microprocessor 38 takes over until the end of the measuring cycle as indicated by time location 52. Also, ADC 36 shifts the data containing the peak interval out of shift register 34 and into the digital memory of microprocessor 38.

Another embodiment of the flow measurement apparatus utilizes an alternative implementation of analog correlator 30, i.e., SAW correlator. A limitation of the SAW technology arises when the SAW device is operated at frequencies below 10 MHz due to the need to keep the dimension of the SAW device larger than the acoustic wavelength in the SAW material. The limitations of the ultrasonic transit time measurement require that the signal frequencies be about 1 MHz so the use of a SAW device would require large sizes of piezoelectric material. In order to avoid this problem an alternate scheme is available to implement a SAW correlator. The electrical received analog signal is amplified such that the oscillating signal becomes a square wave changing sign at every zero-crossing of the signal. This squarewave signal can phase modulate a higher frequency carrier signal by driving a mixer with the square wave and the higher frequency. In this manner the code of the 1 MHz ultrasonic signal is transformed into a phase shift code on the carrier signal. The carrier signal is fed into a SAW correlator device designed to operate at the higher carrier frequency. The size of the SAW material is now small since it is controlled by the higher carrier frequency and not the ultrasonic lower frequency. All other attributes of the BBD correlator described above hold for this alternate implementation of a SAW correlator.

An additional modification to the means of exciting the transmitting transducer can be implemented to improve the use of the correlation detection technique to measure ultrasonic transit time flow. When a pulse excites an ultrasonic transducer the transducer has a tendency to ring at it natural frequency unless it is dampened. Ringing will cause an interference with the detection of the code imparted to the transmitted ultrasonic signal. In order to reduce the effect of ringing the code that is modulated with the transmission signal may be spread out. The coded transmission signal consists of a single cycle of phase followed by a delay to allow the ringing to dampen out. Thereafter, there are subsequent single cycles of the appropriate phase followed by a delay until all of the coded transmission signal is transmitted. This technique will avoid the interference with ringing but the total time required to impart the code will be longer due to the extra delays. In order to reduce the total time of transmitting the coded transmission signal, a second single pulse that is 180 degrees out-of-phase with the transmit pulse follows each single pulse, thus reversing the oscillator and canceling the ringing. Such a modification to the transmission signal provides ringing reduction and hence correlation peak enhancement to allow the detection of the peak interval and limit the data required for transit time determination.

It is contemplated that the preferred embodiment and alternative embodiments, described above, may be used on any type of flow measuring device that would benefit from low energy consumption, such as any device which uses a 4–20 ma two wire loop. In a 4–20 ma circuit the measurement variable is represented by 4 ma when it is at its zero point and 20 ma when it is at full scale. A transmitter circuit is usually divided into two parts, i.e., one that performs the measurement and one that controls the current in the two wire loop. Standard practice is to use a fixed amount of current, independent of the process variable, for the measurement circuit of the transmitter. The measurement circuit uses 4 ma or less whether the measurement is close to zero or close to full scale. Only the current control portion of the output circuit changes the total current from 4 ma at zero to 20 ma at full scale. By deviating from common practice the measurement can be improved. For a 4–20 ma two wire loop, in particular, current in excess of 4 ma, which is being transmitted over the two wires when the measurement variable is not zero, can be used to increase the power used in the measurement portion of the circuit.

Current in excess of the 4 ma zero point current may be used when the measurement is at a non-zero value. For the ultrasonic flow meter, the additional current is available to take more samples of transit time measurement and thus obtain better data averaging. When limited to the 4 ma current, the number of samples is limited in order to fit within the energy budget provided by the 4 ma. When operating at non-zero, more current is available and the number of samples could be increased. Since non-zero measurement is normally the case, i.e., the meter is generally in a non-zero state, then the measurement accuracy could be improved for most of its operation. In addition, flow noise is worse when the flow is highest. By utilizing the extra current at these times, the extra current is available for better data averaging and noise reduction.

The use of the measuring apparatus of the present invention is primarily intended, but not limited to, the measurement of flow rates in a pipe or conduit. Additional applications of the low power techniques of the present invention are also possible for the measurement of other parameters or physical properties based upon a determination of the transit time of an ultrasonic pulse.

Figure 4:
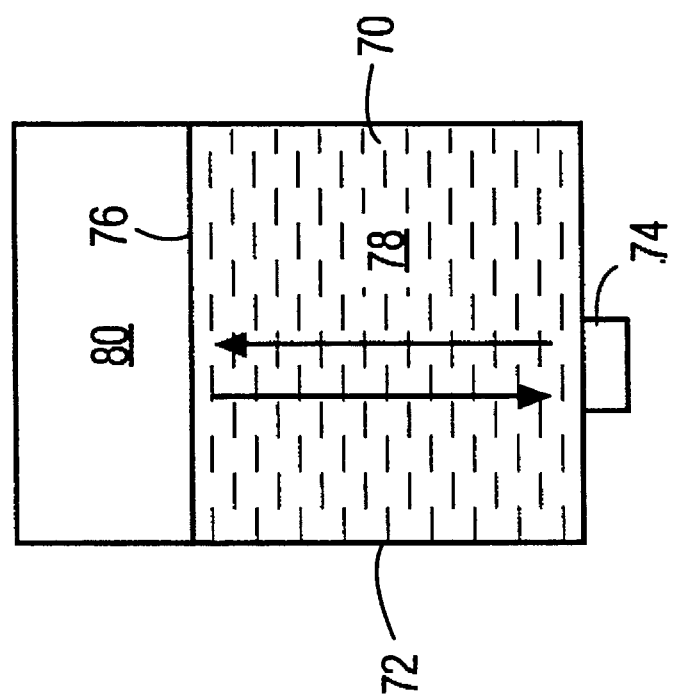
FIG. 4 is a schematic representation of fluid storage tank which incorporates the measurement apparatus of the present invention to measure the level of fluid contained within the tank.

FIG. 4 describes one such other embodiment according to the present invention wherein the level of a fluid medium is measured using the lower power techniques of the present invention based upon a determination of the transit time of an ultrasonic pulse. According to FIG. 4, the level of a fluid medium 70 which is contained within a tank, vessel or container 72 can be determined by measuring the transit time of a pulse generated from transducer 74 from a fixed point to gas/liquid phase interface 76. In accordance with the embodiment shown in FIG. 4 transducer 74 is disposed about the bottom of tank 72 such that the pulse generated from transducer 74 travels through fluid medium 78 until it reached gas/liquid interface 76 where the pulse is deflected and returned to transducer 74 or a separate receiving transducer (not shown) which replaces transducers 16 and/or 18 of FIG. 1. The returned or deflected pulse is received by transducer 74 as an electrical received analog signal. Alternatively, transducer 74 could be disposed about the top of tank 72 such that the pulse generated thereby travels through gas 80 until it reaches gas/liquid interface 76 where the pulse is similarly deflected and returned to transducer 74 or a separate receiving transducer (not shown). In either case, the position of phase interface 76 is determined by measuring the transit time a pulse from a fixed point to the interface. As the level of the liquid or gas phase changes so will the position of phase interface 76 change and this change in the position of phase interface 76 is measured through the transit time of the ultrasonic pulse knowing the velocity in the fluid medium or gas through which it traverses, i.e., distance equals time divided by velocity. By using the energy management technique of the present invention a level measurement could be performed in a low power mode and be operated from a two wire 4–20 milliamp line.

The pulse which is either returned to transducer 74 or a separate receiver transducer is then processed via a correlator such as a BBD, CCD or SAW correlator which correlates the received analog signal with the ultrasonic transmission signal such that peak interval of the received analog signal is detected.

Figure 5:
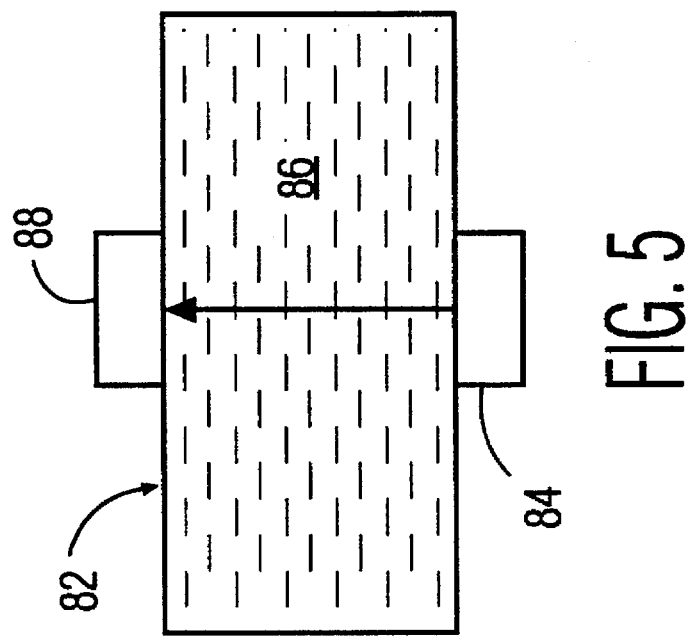
FIG. 5 is a schematic representation of a container which incorporates the measurement apparatus of the present invention to measure the velocity in a binary mixture to determined the compositional make-up of the binary mixture.

In accordance with still another embodiment, FIG. 5 depicts an apparatus according to the present invention which can be used to measure the velocity in a binary mixture of a fluid medium or gas where the velocity would determine the proportion of each component in the binary mixture. By using the power management techniques of the present invention this measurement could be a two wire low power measurement. According to FIG. 5, a tank, vessel, container, conduit or the like 82 contains either a binary mixture of a fluid medium or gas, wherein a pulse generated from signal generating transducer 84 is sent through binary mixture 86 and the electric received analog signal is received by transducer 88 which is disposed opposite to the signal generating transducer 84 which replaces transducers 16 and/or 18 in FIG. 1.

As such, the use of the measuring apparatus according to the present invention would allow for low power measurement of the velocity in fluids or gases to determine the physical properties of the fluid. In this case the distance would be a known constant and the transit time would be used to determine the velocity in the fluid or gas, i.e., velocity equals distance divided by transit time. The compositional make-up of binary mixture 86 would be determined by detecting the velocity of the fluid or gas.

Figure 6:
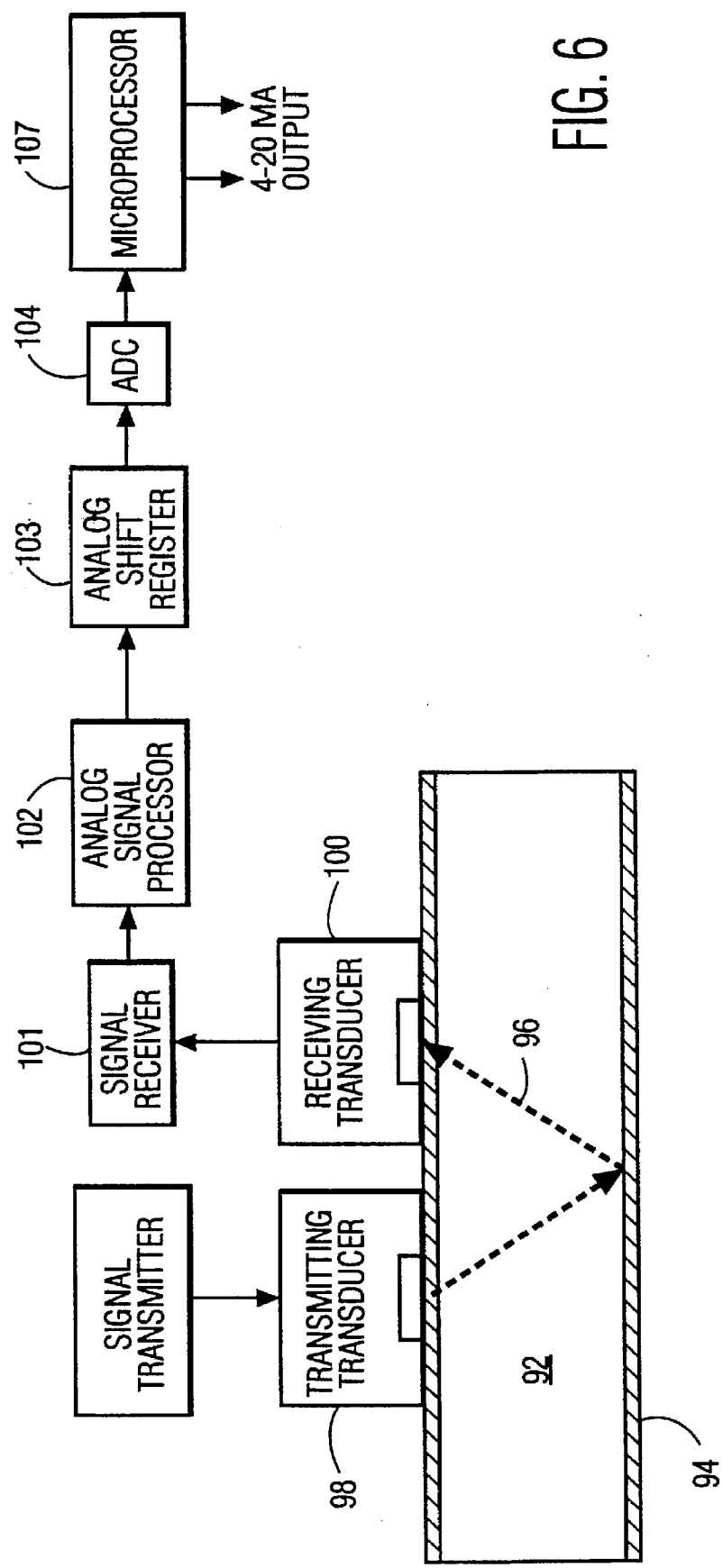
FIG. 6 is a block diagram of another embodiment according to the present invention wherein any wave or signal is passed through a medium and thereafter processed by an analog signal processor prior to analog-to-digital conversion and microprocessing of the digitized signal.

FIG. 6 depicts another embodiment of the present invention wherein a low power apparatus 90 for measuring various physical properties of a fluid or gas medium 92 contained within conduit, pipe, vessel, tank, etc. 94 by measuring the change of a wave signal or time dependent signal 96 as it traverses fluid or gas medium 92. Low power apparatus 90 comprising: at least one transmission means 98 (i.e., a transducer) for providing a transmitted wave or time dependent signal for injection into the fluid or gas medium; at least one reception means 100 (i.e., a transducer), displaced from transmission means 98 for receiving a received wave or time dependent signal from fluid or gas medium 92; and means, coupled to the reception means, for analog signal processing of the received wave or time dependent signal such that a short interval of the processed received wave or time dependent signal is extracted. The means for analog signal processing comprises a signal receiver 101, analog signal processor 102 (e.g., an analog correlator) and analog shift register 103. The desired output peak from analog shift register 103 is then sent to ADC 105 for conversion of the analog signal peak to digitized data. The digitized data is thereafter sent to microprocessor 107 to provide for the measurement of the desired physical properties of the gas or fluid process medium through which signal 96 traveled.

The invention having been thus described with particular reference to the preferred forms thereof, it will be obvious that various changes and modifications may be made therein without departing from the spirit and scope of the invention as defined in the appended claims.

What is claimed is:

1. An apparatus for measuring flow velocity of a fluid or gas medium by measuring a transit time of an ultrasonic transmission signal through the fluid or gas medium both with and against the flow of said fluid or gas medium, the apparatus comprising:

a first transmission means for providing a first ultrasonic transmission signal for injection into said fluid or gas medium in the direction of the flow at a predetermined time;

a first reception means, displaced from said first transmission means, for receiving a first ultrasonic received analog signal from said fluid or gas medium;

a second transmission means for providing a second ultrasonic transmission signal for injection into said fluid or gas medium in the direction against the flow at a predetermined time;

a second reception means, displaced from said second transmission means, for receiving a second ultrasonic received analog signal from said fluid or gas medium;

means, coupled to both said first and second reception means, for correlating said first and second ultrasonic received analog signals with said first and second ultrasonic transmission signals, respectively, such that peak intervals of the correlation of both said first and second ultrasonic received analog signals are extracted;

an analog-to-digital converter, coupled to said means for correlating, for digitizing said peak intervals; and a processor means, coupled to said analog-to-digital converter, for calculating from said digitized peak intervals the transit time of said fluid or gas medium.

2. The apparatus as defined in claim 1, wherein said first and second transmission means each include a transmitting ultrasonic transducer for sending said first and second ultrasonic transmission signals, respectively, into said fluid or gas medium, and said first and second reception means each include a receiving ultrasonic transducer for receiving said first and second received analog signals, respectively.

3. The apparatus as defined in claim 1, wherein said first transmission means and said second reception means are a first ultrasonic transducer which is capable of both transmitting said first ultrasonic transmission signal and receiving said second ultrasonic received analog signal, and said second transmission means and said first reception means are a second ultrasonic transducer which is capable of both transmitting said second ultrasonic transmission signal and receiving said first ultrasonic received analog signal.

4. The apparatus as defined in claim 3 further comprising a switching means which enables said first ultrasonic transducer to act as said first transmission means when said second ultrasonic transducer acts as said first reception means, and also enables said first ultrasonic transducer to act as said second reception means when said second ultrasonic transducer acts as said second transmission means.

5. The apparatus as defined in claim 1, wherein said means for correlating comprises an analog correlator for correlating said first and second ultrasonic received analog signals with said first and second ultrasonic transmission signals, respectively.

6. The apparatus as defined in claim 5, wherein said analog correlator is capable of generating a peak output having a peak interval based on an alignment of said first and second ultrasonic received analog signals with said first and second ultrasonic transmission signals.

7. The apparatus as defined in claim 5, wherein said analog correlator is selected from the group consisting of: a bucket brigade device, a charge coupled device and a surface acoustic wave device.

8. The apparatus as defined in claim 6, wherein said means for correlating further comprises an analog shift register, coupled to said analog correlator, for extracting said peak interval from said peak output.

9. The apparatus as defined in claim 8, wherein said means for correlating further comprises a peak detector, responsive to said peak interval, for signaling to said analog shift register to extract a particular time period of said peak output, wherein said particular time period includes said peak interval.

10. The apparatus as defined in claim 9, wherein said peak detector includes a stop counter for determining a peak time when said peak interval is detected and signaling said peak time to said analog shift register.

11. The apparatus as defined in claim 1, further comprising a delay counter for delaying the activation of said means for correlating, said analog-to-digital converter and said processor means for a set delay time to conserve energy.

12. The apparatus as defined in claim 11, wherein the time period of said set delay time is determined by said processor means and is dependent on the size of the passage through which the fluid or gas medium travels.

13. The apparatus as defined in claim 1, further comprising a clock timer provides timing to said first and second transmission means and said means for correlating.

14. The apparatus as defined in claim 9, wherein said ultrasonic transmission signal comprises a first pulse followed by a second pulse that is 180 degrees out-of-phase, whereby noise received by said first or second reception means is canceled.

15. The apparatus as defined in claim 1 further comprising a 4 to 20 milliamp two wire loop which is used to supply energy to said apparatus for measuring process parameters of a fluid or gas medium.

16. The apparatus as defined in claim 15, wherein said apparatus for measuring process parameters of a fluid or gas medium uses only 4 milliamps when operating at close to zero point or close to full scale, thereby leaving a residual current in the amount of 16 milliamps to be used to drive said apparatus for measuring process parameters of a fluid or gas medium to take more samples of transit time measurement.

17. The apparatus as defined in claim 1 wherein said first and second ultrasonic transmission signals are wave or time dependent signals.

* * * * *